United States Patent
Hasegawa et al.

(10) Patent No.: US 10,302,564 B2
(45) Date of Patent: May 28, 2019

(54) WATER QUALITY ANALYZER

(71) Applicant: FUJI ELECTRIC CO., LTD., Kawasaki-shi, Kanagawa (JP)

(72) Inventors: Yoshiki Hasegawa, Kawasaki (JP); Kazuhiro Koizumi, Kawasaki (JP)

(73) Assignee: FUJI ELECTRIC CO., LTD., Kawasaki-Shi, Kanagawa (JP)

( * ) Notice: Subject to any disclaimer, the term of this patent is extended or adjusted under 35 U.S.C. 154(b) by 0 days.

(21) Appl. No.: 15/968,409

(22) Filed: May 1, 2018

(65) Prior Publication Data
US 2018/0246035 A1  Aug. 30, 2018

Related U.S. Application Data

(63) Continuation of application No. PCT/JP2017/006951, filed on Feb. 23, 2017.

(30) Foreign Application Priority Data

May 19, 2016 (JP) ................................. 2016-100435

(51) Int. Cl.
*G01N 21/47* (2006.01)
*G01N 21/49* (2006.01)
(Continued)

(52) U.S. Cl.
CPC ............. *G01N 21/64* (2013.01); *G01N 21/49* (2013.01); *G01N 21/532* (2013.01);
(Continued)

(58) Field of Classification Search
None
See application file for complete search history.

(56) References Cited

U.S. PATENT DOCUMENTS 5,123,731 A * 6/1992 Yoshinaga ......... G01N 15/0205
250/461.2
5,260,764 A * 11/1993 Fukuda .................. G01N 15/14
250/458.1

(Continued)

FOREIGN PATENT DOCUMENTS

JP H3-233344 A 10/1991
JP 08145889 A * 6/1996
(Continued)

OTHER PUBLICATIONS

Tucker S A et al: "Primary and Secondary Inner Filtering"; Effect of K2Cr2O7 on fluorescence emission intensities of quinine sulfate. Journal of Chemical Education, American Chemical Society, US, vol. 69, No. 1, 1992, pp. A8-A12, XP008108872, ISSN: 0021-9584, DOI: 10.1021/ed069pA8.

*Primary Examiner* — Andrew Smyth
(74) *Attorney, Agent, or Firm* — Rabin & Berdo, P.C.

(57) ABSTRACT

A water quality analyzer for analyzing sample water. The water quality analyzer includes an excitation light irradiating optical system configured to irradiate the sample water with first light, a component in the sample water being excited by the first light to emit fluorescence, a scattered light irradiating optical system configured to irradiate the sample water with second light, the second light being scattered by microparticles in the sample water to form the scattered light, a fluorescence detecting optical system configured to detect a portion of the second light that has passed through the sample water, and to detect the emitted fluorescence, and a scattered light detecting optical system configured to detect a portion of the first light that has passed through the sample water, and to detect the scattered light.

13 Claims, 8 Drawing Sheets

(51) Int. Cl.
- *G01N 21/53* (2006.01)
- *G01N 21/64* (2006.01)
- *G01N 33/18* (2006.01)
- *G01N 21/3577* (2014.01)

(52) U.S. Cl.
CPC .......... *G01N 21/645* (2013.01); *G01N 33/18* (2013.01); *G01N 33/1893* (2013.01); *G01N 21/3577* (2013.01); *G01N 2021/4726* (2013.01); *G01N 2021/6491* (2013.01)

(56) References Cited

U.S. PATENT DOCUMENTS

| | | | | |
|---|---|---|---|---|
| 5,489,977 | A * | 2/1996 | Winslow | G01N 21/53 356/339 |
| 6,407,383 | B1 * | 6/2002 | Byatt | G01N 33/1833 250/301 |
| 2003/0058450 | A1 * | 3/2003 | Mosley | G01N 21/3151 356/436 |
| 2011/0186753 | A1 * | 8/2011 | Dixon | G01J 1/58 250/459.1 |
| 2016/0103089 | A1 * | 4/2016 | Boyette | G01N 27/27 137/3 |

FOREIGN PATENT DOCUMENTS

| | | |
|---|---|---|
| JP | H08-145889 A | 6/1996 |
| JP | 2005-091095 A | 4/2005 |
| JP | 2005-536713 A | 12/2005 |
| JP | 2009-236832 A | 10/2009 |
| JP | 2012-118046 A | 6/2012 |
| JP | 2012118046 A * | 6/2012 |

\* cited by examiner

WATER QUALITY ANALYZER

CROSS-REFERENCE TO RELATED APPLICATION

This application is a continuation application of International Application PCT/JP2017/006951, filed on Feb. 23, 2017, which claims priority to Japanese Patent Application No. 2016-100435, filed on May 19, 2016, the entire contents of which are incorporated herein by reference.

BACKGROUND OF THE INVENTION (1) Technical Field

The present invention relates to a water quality analyzer for measuring the components of the sample water to be measured.

(2) Background Art

For a water quality analyzer based on the principle of fluorescence detection, those analyzer that detects the fluorescence emitted from an excited specific component in sample water to be measured and analyzes water quality has been generally known. This water quality analyzer irradiates sample water in a sample cell with excitation light from a light source and excites a specific component, then collects the light with a specific wavelength by passing the resulting emitted light through an optical filter and detects the fluorescence by introducing the light having a specific wavelength into a fluorescence detector. In such a water quality analyzer, an optical path of an irradiating system from a light source to a sample cell and an optical path of a detecting system from the sample cell to a detector are arranged to cross perpendicularly each other in order to prevent the direct introducing of the light from the light source into the detector (see, for example, Japanese Unexamined Patent Application Publication No. 8-145889).

SUMMARY OF INVENTION

Incidentally, because the fluorescence intensity of a component in sample water is known to be decreased when the sample water is turbid (high turbidity), it is necessary to measure the turbidity in order to measure the fluorescence intensity of the sample water with high accuracy. A turbidity meter based on the principle of light scattering detection measures turbidity by irradiating a sample cell containing sample water to be measured with light having a specific wavelength emitted from a light source and detecting the light scattered by microparticles contained in the sample water as suspending materials by using a scattered light detector.

In recent, in order to measure fluorescence intensity and turbidity of sample water simultaneously, there is increasing demand for a water quality analyzer having both fluorescence detecting function and scattered light detecting function. A water quality analyzer having fluorescence detecting function combined with scattered light detecting function is required to comprise a light source and a detector for excitation as well as a light source and a detector for scattered light detection. In addition to, in order to ensure stable measurements of the water quality analyzer, it is desirable to monitor the decrease in light amount of each light source.

However, such water quality analyzer leads to complicated configuration, by adding additional functions. For example, for the water quality analyzer having fluorescence detecting function combined with scattered light detecting function, in order to measure light amount of each light source, each light source shall comprise a light amount detector, and it causes a problem of complicated configuration.

The present invention provides a water quality analyzer having a fluorescence detecting function combined with a scattered light detecting function as an additional function in simple configuration and can measure fluorescence intensity of sample water with high accuracy.

The water quality analyzer of the present invention includes an excitation light irradiating optical system configured to irradiate a sample water to be measured with light source light for excitation, a fluorescence detecting optical system configured to detect fluorescence emitted from a specific component in the sample water excited by the irradiating with the light source light for excitation, a scattered light irradiating optical system configured to irradiate the sample water with the light source light for scattered light detection, and a scattered light detecting optical system configured to detect scattered light scattered by microparticles in the sample water by the irradiation with the light source light for scattered light detection, wherein the fluorescence detecting optical system is configured to detect an amount of the light emitted from the scattered light irradiating optical system, and the scattered light detecting optical system is configured to detect an amount of the light emitted from the excitation light irradiating optical system.

By this configuration, the analyzer can measure the fluorescence intensity of the sample water with high accuracy while taking the effect of the sample water turbidity into consideration, because the fluorescence is detected by the fluorescence detecting optical system while detecting the scattered light by the scattered light detecting optical system. In addition, the analyzer can monitor the light amount of the excitation light source in the scattered light detecting optical system without providing a dedicated light amount detector because the scattered light detecting optical system can detect the light amount of the excitation light source when monitoring the light amount of the excitation light source. The analyzer can monitor the light amount of the light source for the scattered light detection in the fluorescence detection optical system without providing a dedicated light amount detector, because the fluorescence detecting optical system can also detect the light amount of the light source for scattered light detection when monitoring the light amount of the light source for scattered light detection. Thereby, the analyzer can perform stable water quality analysis in consideration of the decrease of the light amounts of the light sources for excitation and scattered light detection.

The water quality analyzer of the present invention includes an excitation light irradiating optical system configured to irradiate a sample water to be measured with light source light for excitation, a fluorescence detecting optical system configured to detect fluorescence emitted from a specific component in the sample water excited by the irradiation with the light source light for excitation, a scattered light irradiating optical system configured to irradiate the sample water with light source light for scattered light detection, a scattered light detecting optical system configured to detect scattered light scattered by microparticles in the sample water by the irradiation with the light source light for scattered light detection, wherein the water quality analyzer configured to detect an amount of the light emitted from the excitation light irradiating optical system and an amount of the light emitted from the scattered light irradiating optical system, and a transmitted light detecting optical system configured to detect a first transmitted light that is the light source light for excitation that has passed through the sample water and a second transmitted light that is the light source light for scattered light detection that has passed through the sample water, and a predict part configured to calculate an absorbance of the sample water at a first wavelength of the light source light for excitation from the first transmitted light, and calculate an absorbance of the sample water at a second wavelength of the light source light for scattered light detection from the second transmitted light, and predict an absorbance of the sample water at a third wavelength of the fluorescence from the absorbances of sample water at the first wavelength and the second wavelength.

By this configuration, the absorbances of the sample water at the first and the second wavelength are calculated based on the transmitted light of the light source light for excitation having the first wavelength and the transmitted light of the light source light for scattered light detection having the second wavelength. Absorbance of the fluorescence at the third wavelength is predicted using these absorbances and the fluorescence absorbance at the third wavelength is used for correction of fluorescence intensity. Thereby, the fluorescence intensity can be measured with high accuracy and the configuration of the water quality analyzer can be simplified because it is not required to install a light source that irradiates light having the third wavelength for correction of fluorescence intensity in the water quality analyzer and not to measure absorbance of sample water at the third wavelength.

According to the present invention, the water quality analyzer can obtain both fluorescence detecting function and scattered light detecting function as an additional function in simple configuration and can measure the fluorescence intensity of sample water with high accuracy.

DESCRIPTION OF EMBODIMENTS

Figure 1:
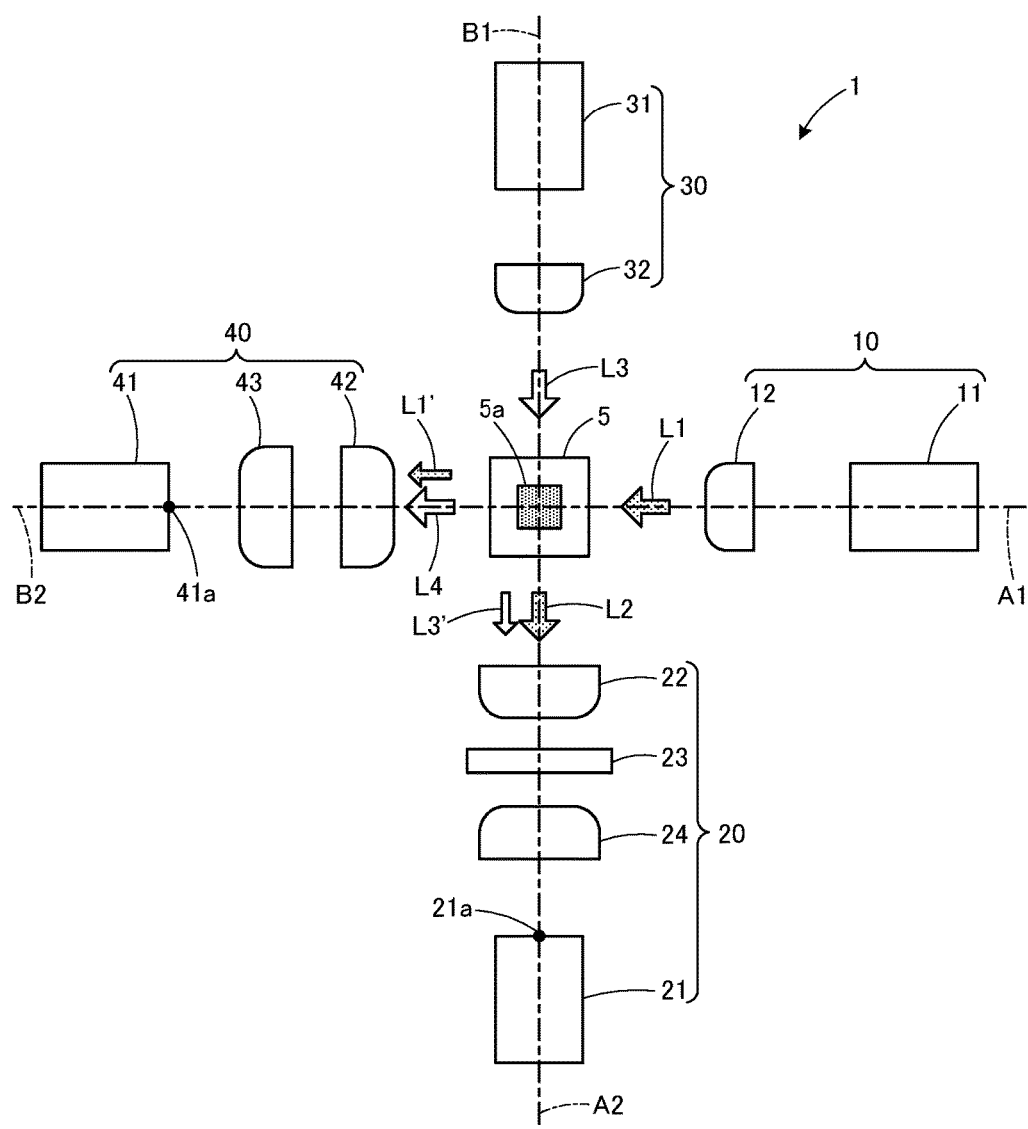
FIG. 1 shows a schematic block diagram of the water quality analyzer according to the first embodiment.

The water quality analyzer according to the first embodiment of the present invention is explained in detail below. FIG. 1 is a schematic block diagram of the water quality analyzer according to the first embodiment of the invention.

The water quality analyzer 1 comprises an excitation light irradiating optical system 10, a fluorescence detecting optical system 20, a scattered light irradiating optical system 30, and a scattered light detecting optical system 40 in the four directions around a sample cell 5. The excitation light irradiating optical system 10 and the scattered light detecting optical system 40 are arranged so as to be opposed to each other across the sample cell 5, and the scattered light irradiating optical system 30 and the fluorescence detecting optical system 20 are arranged so as to be opposed to each other across the sample cell 5. At the center of the sample water channel 5a of the sample cell 5, the optical axis A1 of the excitation light irradiating system 10 and the optical axis A2 of the fluorescence detecting optical system 20 are arranged so as to cross perpendicularly each other and the optical axis B1 of the scattered light irradiating optical system 30 and the optical axis B2 of the scattered light detecting optical system 40 are arranged so as to cross perpendicularly each other.

The excitation light irradiation optical system 10 has an excitation light source 11 and a collimator lens 12 arranged between the light source 11 and the sample cell 5. The fluorescence detecting optical system 20 has a fluorescence detector 21, a condensing lens 22 arranged between the fluorescence detector 21 and the sample cell 5, an optical filter 23, and a condensing lens 24. The condensing lenses 22, 24 are symmetrically arranged with convex surfaces facing the optical filter 23. The scattered light irradiating optical system 30 has a light source for scattered light detection 31 and a collimator lens 32 arranged between the light source 31 and the sample cell 5. The scattered light detecting optical system 40 has a scattered light detector 41 and condensing lenses 42, 43 arranged between the scattered light detector 41 and the sample cell 5. The condensing lenses 42, 43 are arranged with each convex surface facing outside.

The sample cell 5 is formed into a rectangular cylindrical shape having the sample water channel 5a at the center, extending perpendicular to the optical axes A1, A2, B1 and B2. Sample water to be measured are made to flow through the sample water channel 5a. As the sample cell, a flow cell made of a transparent material such as quartz glass is used, but a rectangular cell made of quartz glass can be also used. As the light source 11 and the light source 31, those which emits light having a specific wavelength, such as a light emitting diode and laser diode, can be used. As the fluorescence detector 21 and the scattered light detector 41, a photo diode, a photomultiplier tube, and the like, can be used. As the optical filter 23, an optical element having a function to pass only light having a specific wavelength and to cut other lights and of which cutting ratio is less than 100% is used, but not limiting hereto.

In this configuration, the excitation light source 11 and the light source for scattered light detection 31 are lighted when measuring sample water. Real samples are made to flow through the sample water channel 5a of the sample cell 5. From the excitation light source 11, light source light for excitation L1 is emitted and the light source light L1 passes through the collimator lens 12, becomes nearly parallel light (collimator light) and irradiates sample water in the sample cell 5. Components to be detected in the sample water is excited by the light source light L1 and emits fluorescence L2. Fluorescence L2 is condensed by a condensing lens 22, reaches an optical filter 23, and condensed by a condensing lens 24 after extracting light having a specific wavelength by the optical filter 23, and reaches a light receiving surface 21a of a fluorescence detector 21. A part of the light source light L1 advances straightly in the sample cell 5, passes through the sample cell 5 and is condensed as transmitted light L1' by the condensing lenses 42, 43, and then reaches a light receiving surface 41a of a scattered light detector 41.

The light source for scattered light detection 31 emits light source light for scattered light detection L3 and the light source light L3 passes through the collimator lens 32 and becomes nearly parallel light, and then irradiates the sample water in the sample cell 5. The light source light L3 is scattered by microparticles as suspending materials contained in the sample water and scattered light L4 is emitted therefrom. The scattered light L4 is condensed by the condensing lenses 42, 43 and reaches the light receiving surface 41a of the scattered light detector 41. A part of the light source light L3 advances straightly in the sample cell 5, passes through the sample cell 5 and be condensed as the transmitted light L3' by the condensing lens 22, and then reaches the optical filter 23. A major part of the transmitted light L3' is removed by the optical filter 23 but a part of the transmitted light L3' passes though the optical filter 23 and is condensed by the condensing lens 24 and reaches the light receiving surface 21a of the fluorescence detector 21.

Subsequently, when monitoring the light amount of the excitation light source 11, the excitation light source 11 is switched on and the light source for scattered light detection 31 is switched off. In the sample water channel 5a of the sample cell 5, water containing no fluorescent and light scattered component (pure water) is made to flow. The light source light L1 emitted from the light source 11 passes through the collimator lens 12 and irradiates the sample cell 5. The light source light L1 passes through the sample cell 5, is condensed as the transmitted light L1' by the condensing lenses 42, 43, and reaches the light receiving surface 41a of the scattered light detector 41 and the transmitted light L1' is detected.

When monitoring the light amount of the light source 31 for scattered light detection 30, the excitation light source 11 is switched off and the light source for scattered light detection 31 is switched on. In the sample water channel 5a of the sample cell 5, pure water is made to flow. The light source light L3 emitted from the light source 31 passes through the collimator lens 32 and irradiates the sample cell 5. The light source light L3 passes through the sample cell 5, is condensed as the transmitted light L3' by the condensing lens 22, and reaches the optical filter 23. A part of the transmitted light L3' through the optical filter 23 is condensed by the condensing lens 24 and reaches the light receiving surface 21a of the fluorescence detector 21 and the transmitted light L3' is detected.

Thus, in the water quality analyzer 1, when measuring sample water, the fluorescence intensity is measured by irradiating the sample cell 5 with the light source light for excitation L1 from the excitation light source 11 and detecting the fluorescence L2 emitted from the specific component in the sample water excited by the light source light L1 by using the fluorescence detector 21. At the same time, the turbidity is measured by irradiating the sample cell 5 with the light source light for scattered light detection L3 from the light source for scattered light detection 31 and detecting the scattered light L4 scattered by microparticles in the sample water irradiated with light source light L3 by the scattered light detector 41. The fluorescence intensity can be measured with high accuracy considering the influence of turbidity because the fluorescence is detected while detecting scattered light.

The optical systems 10, 20, 30, 40 are arranged so that the optical axis A1 of the excitation light irradiating optical system 10 and the optical axis A2 of the fluorescence detecting optical system 20 cross orthogonally and the optical axis B1 of the scattered irradiating optical system 30 and the optical axis B2 of the scattered light detecting optical system 40 cross orthogonally at the center of the sample water channel 5a of the sample cell 5. Thereby, the fluorescence L2 emitted from the specific component in the sample water can be detected by the fluorescence detector 21 while suppressing introduction of the transmitted light L1' into the fluorescence detector 21. Also, the fluorescence L4 emitted from the microparticles in the sample water can be detected by the scattered light detector 41 while suppressing introduction of the transmitted light L3' into the scattered light detector 41.

In the water quality analyzer 1, the scattered light detector 41 can also detect the transmitted light L1' that is the light source light L1 passed through the sample cell 5 because the excitation light source 11 and the scattered light detector 41 are arranged opposite to each other. The fluorescence detector 21 can detect the transmitted light L3' that is the light source light L3 passed through the sample cell 5 because the light source for scattered light detection 31 and the fluorescence detector 21 are arranged opposite to each other.

Thus, when monitoring the light amount of the excitation light source 11, the light amount of the excitation light source 11 can be monitored by irradiating the sample cell 5 with the light source light for excitation L1 from the excitation light source 11 and detecting the transmitted light L1' passed through the sample cell 5 by the scattered light detector 41. And, when monitoring the light amount of the light source for scattered light detection 31, the light amount of light source for scattered light detection 31 can be monitored by irradiating the sample cell 5 with the light source light for scattered light detection L3 from the light source for scattered light detection 31 and detecting the transmitted light L3' passed through the sample cell 5 by the scattered light detector 21.

Incidentally, when measuring sample water, not only the fluorescence L2 emitted from a specific component in sample water which is excited by the light source light L1 from the light source 11 but also the transmitted light L3' that is the light source light L3 passed through the sample water enter the fluorescence detector 21 of the fluorescence detecting optical system 20. In the same way, not only the scattered light L4 that is the light source light L3 from the light source 31 scattered by microparticles in the sample water but also the transmitted L1', the light source light L1 passed through the sample water enter the scattered light detector 41 of the scattered light detecting optical system 40.

When measuring the light amounts of the light source 11, 31, in order to improve the detection efficiency of the detectors 41, 21 of the transmitted light L1', L3', the optical axis B1 of the scattered light irradiating optical system 30 shall be aligned with the optical axis A2 of the fluorescence detecting optical system 20 and the optical axis Z1 of the excitation light irradiating optical system 10 shall be aligned with the optical axis B2 of the scattered light optical system 40 in the sample cell 5. However, as described above, when the intensity of the transmitted light L3' is much higher than that of the fluorescence L2, the detection accuracy of the fluorescence detector 21 for the fluorescence L2 may deteriorate because the fluorescence 21 and the transmitted light L3' enter the fluorescence detector 21 when measuring sample water. In the same way, when the intensity of the transmitted light L1' is much higher than that of the scattered light L4, the detection accuracy of the scattered detector 41 for the scattered light L4 may deteriorate because the scattered light L4 and the transmitted light L1' enter the scattered light detector 41.

Therefore, in the water quality analyzer 1 according to the first embodiment, the light amounts of the transmitted lights L3', L1' introduced into the detectors 21, 41 are controlled by adjusting the distance between the intersection point between the optical axis A1 of the excitation light irradiating optical system 10 and the optical axis A2 of the fluorescence detecting optical system 20 and between the optical axis B1 of the scattered light irradiating optical system 30 and the optical axis B2 of the scattered light detecting optical system 40.

Figure 2:
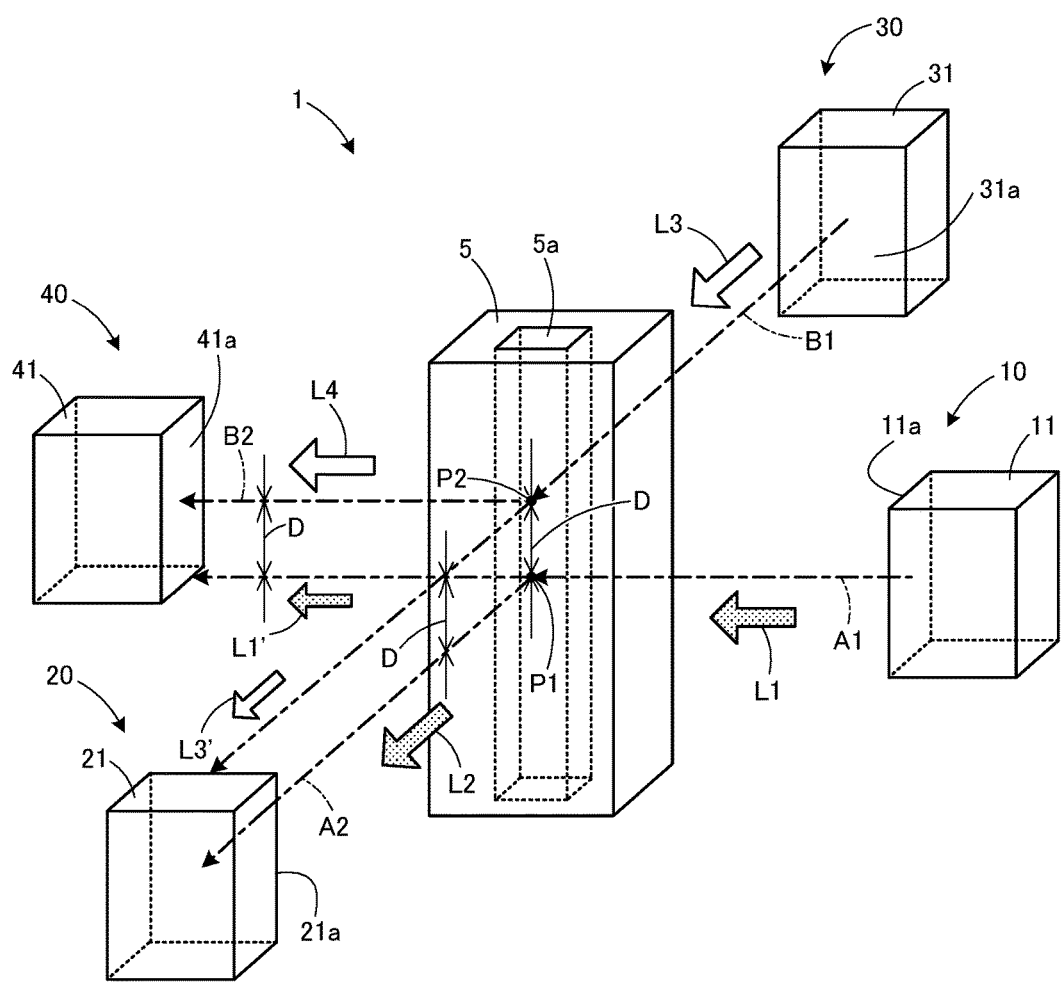
FIG. 2 shows an explanation drawing for describing the light amount adjustment method of transmitted light introduced in each detector according to the first embodiment.

FIG. 2 is an explanation diagram showing a method for adjusting the transmitted light amount introduced into each detector according to the first embodiment. As FIG. 2 shows, the intersection point P1 between the optical axis A1 of the excitation light irradiating optical system 10 and the optical axis A2 of the fluorescence detecting optical system 20 and the intersection point P2 between the optical axis B1 of the scattered light irradiating optical system 30 and the optical axis B2 of the scattered light detecting optical system 40 are configured to be arranged in the sample cell 5 with a distance D mutually. Consequently, a plane formed by the optical axis A1 of the excitation light irradiating optical system 10 and the optical axis A2 of the fluorescence detecting optical system 20 and a plane formed by the optical axis B1 of the scattered light irradiating optical system 30 and the optical axis B2 of the scattered light detecting optical system 40 are configured to be arranged in the sample cell 5 with a distance D mutually. Thereby, the transmitted light L'3 that is the light source light L3 passed through the sample cell 5 is introduced into the light receiving surface 21a of the fluorescence detector 21 at the sight with a distance from the optical axis A2 and the transmitted light L'1, the light source light L1 passed through the sample cell 5, is introduced into the light receiving surface 41a of the scattered light detector 41 at the site with a distance from the optical axis B2. In FIG. 2, the intersection point P2 is configured to be located above the intersection point P1, but the intersection point P2 may be configured to be located below the intersection point P1.

In this case, the distance D is, e.g., larger than 0 and 10 mm or below. When the distance is greater than 0 mm, it prevents aligning the transmitted light L3' with the optical axis A2 and the light amount influence of transmitted light L3' which fluorescence detector 21 detects when measuring sample water can be suppressed. It also prevents aligning the transmitted light L1' with the optical axis B and the light amount influence of transmitted light L1' which the fluorescence detector 21 detects when measuring sample water can be suppressed. When the distance is 10 mm or below, the situation that the transmitted light L1' cannot reach the scattered light detector 41 or cannot be detected due to too small amount if it reaches the detector 41 can be prevented and the light amount of the light source 11 can be monitored by detecting the transmitted light L1' at light amount monitoring. The situation that the transmitted light L3' cannot reach the fluorescence detector 21 or cannot be detected due to too small amount if it reaches the detector 21 also can be prevented and the light amount of the light source 31 can be monitored by detecting the transmitted light L3' at light amount monitoring.

Figure 3A:
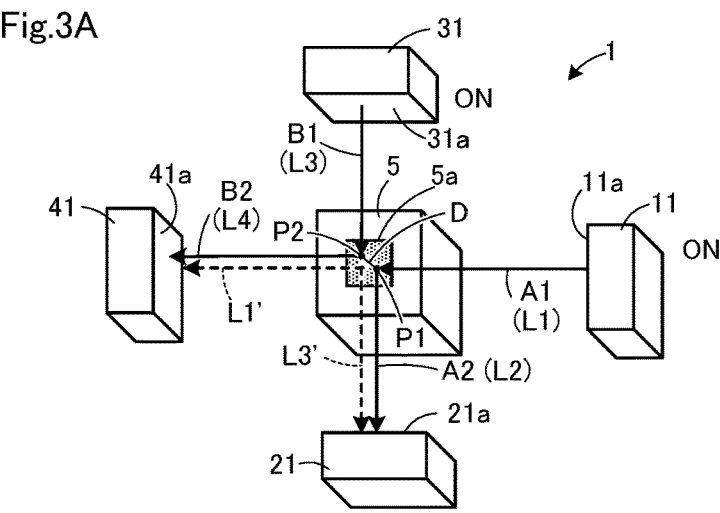
FIGS. 3A, 3B and 3C show explanation drawings for describing the measuring operation of the water quality analyzer according to the first embodiment.
Figure 3B:
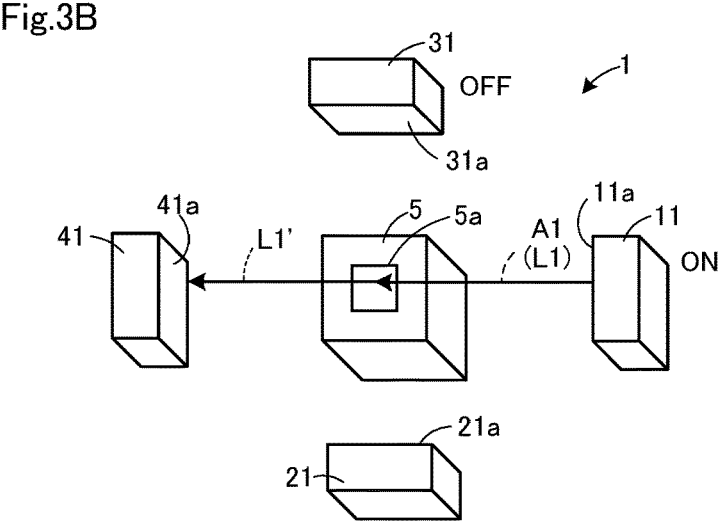
Figure 3C:
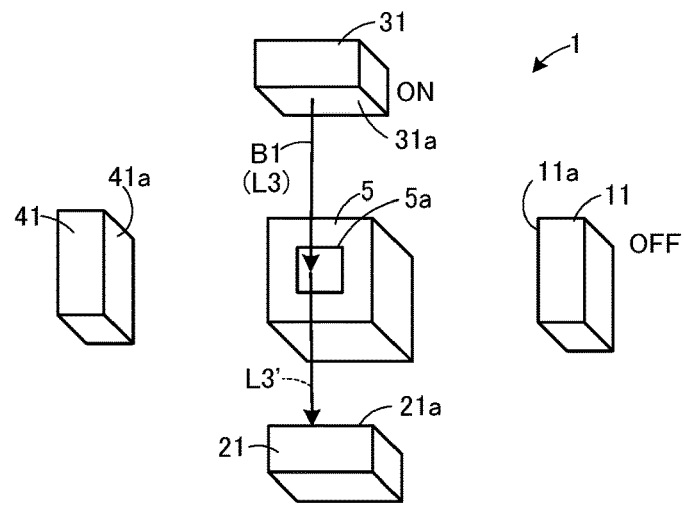

Next, referring FIGS. 3A-3C and Table 1, a measuring operation of sample water by the water quality analyzer 1 according to the first embodiment will be described. FIGS. 3A-3C are explanation drawings for describing the measurement operation of the water quality analyzer according to first embodiment. FIG. 3A is an explanation drawing for describing measurement operations of the fluorescence intensity and turbidity of the sample water according to the first embodiment. FIG. 3B is an explanation drawing for describing detection operations of to the light amount of the excited light irradiating optical system according to first embodiment. FIG. 3C is an explanation drawing for describing the detection operations of to the light amount of the scattered light irradiating optical system according to the first embodiment. Table 1 describes four measurement modes, normal measurement, reference for light amount monitoring, light amount detection of fluorescence light source, and light amount detection of light source for scattered light.

[Table 1]

As shown in FIG. 3A, when measuring sample water, the normal measuring mode in Table 1 is selected and the fluorescence intensity and the turbidity are measured. The real sample is made to flow through the sample water channel 5a of the sample cell 5. Both the excitation light source 11 and the light source for scattered light detection 31 are set to ON state. The excitation light source 11 emits the light source light for excitation L1 and is made to irradiate the water ample in the sample cell 5. The component to be detected in the sample water is excited by the light source light L1 and emits fluorescence L2 and the fluorescence L2 reaches the light receiving surface 21a of the fluorescence detector 21. A part of the light source light L1 advances straightly in the sample cell 5, passes through the sample cell 5 and reaches the light receiving surface 41a of the scattered light detector 41 as the transmitted light L1'.

The light source for scattered light detection 31 emits the light source light for scattered light detection L3 and is made to irradiate the sample water in the sample cell 5. The light source light L3 is scattered by microparticles in the sample water and the scattered light L4 reaches the light receiving surface 41a of the scattered light detector 41. A part of the light source light L3 advances straightly in the sample cell 5 and passes through in the sample cell 5, and then reaches the light receiving surface 21a of the fluorescence detector 21 as the transmitted light L3'. As described above, when measuring sample water, the fluorescence L2 of the real sample and the transmitted light L3' are detected on the light receiving surface 21a of the fluorescence detector 21 and the scattered light L4 of real sample and the transmitted light L1' are detected on the light receiving surface 41a of the scattered light detector.

In this case, by separating the optical axis B1 of the scattered light irradiating optical system 30 from the optical axis A2 of the fluorescence detecting optical system 20 with distance D in the sample cell 5, the transmitted light L3' that is the light source light L3 passed through the sample cell 5 is introduced into the site away from the optical axis A2 on the light receiving surface 21a of the fluorescence detector 21. By separating the optical axis A1 of the scattered light irradiating optical system from the optical axis B2 of the scattered light detecting optical system with distance D in the sample cell 5, the transmitted light L1' that is the light source light L1 passed through the sample cell 5 is introduced into the site away from the optical axis B2 on the light receiving surface 41a of the scattered light detector 41.

Thereby, the influence of the transmitted light L3' detected by the fluorescence detector 21 can be suppressed and the fluorescence detector 21 can detect the fluorescence L2 with high accuracy because the light amount of the transmitted light L3' to be introduced into the fluorescence detecting optical system 20 can be controlled. In addition, because the light amount of the transmitted light L1' to be introduced into the scattered light detecting optical system 40 can be controlled, the influence of the transmitted light L1' detected by the fluorescence detector 41 can be suppressed and the scattered light detector 41 can detect the scattered light L4 with high accuracy.

Although figures are omitted, when measuring background, a reference mode for light amount monitoring is selected, background light amount is detected when the light amount monitoring is performed on the light sources 11, 31. Water containing no fluorescent and scattering components (pure water) is made to flow through the sample cell 5. Both the excitation light source 11 and the light source for scattered light detection 31 are set to the OFF state and the background light amounts are detected by the fluorescence detector 21 and the scattered light detector 41. Because the detectors 21, 41 are generally shaded, the background light amount is nearly null.

As shown in FIG. 3B, when the light amount monitoring is performed on the excitation light source 11, the light amount detection mode for the excitation light source is selected and the transmitted light L1' of the light source 11 is detected. Pure water is made to flow through the sample water channel 5a of the sample cell 5. The excitation light source 11 is set to the ON state and the light source for scattered light detection 31 is set to the OFF state. The light source light L1 emitted from the light source 11 is made to irradiate the sample cell 5. The light source light L1 passes through the sample cell 5 and reaches the light receiving surface 41a of the scattered light detector 41 as the transmitted light L1' and the transmitted light L1' is detected. Because the scattered light detecting optical system 40 (see FIG. 1) is arranged opposite to the excitation light irradiating optical system 10 (see FIG. 1), the transmitted light L1' can be detected and the light amount can be monitored for the light source 11 without installing a dedicated light amount detector.

As shown in FIG. 3C, when monitoring the light amount of the light source for scattered light detection 31, the light amount detection mode for the light source for scattered light detection is selected and the transmitted light L3' of the light source 31 is detected. Pure water is made to flow through the sample water channel 5a of the sample cell 5. The excitation light source 11 is set to the OFF state and the light source for scattered light detection 31 is set to the ON state. The light source light L3 emitted from the light source 31 is made to irradiate the sample cell 5. The light source light L3 passes through the sample cell 5 and reaches the light receiving surface 21a of the fluorescence detector 21 as the transmitted light L3' and the transmitted light L3' is detected. Because the fluorescence detecting optical system 20 (see FIG. 1) is arranged opposite to the scattered light irradiating optical system 30 (see FIG. 1), the transmitted light L3' can be detected and the light amount can be monitored for the light source 31 without installing a dedicated light amount detector.

By monitoring the light amounts of the light source 11, 31, a feedback control in which decreases in light amounts due to deteriorations of the light sources 11, 31 are detected and the light amounts can be kept constant as well as a correction procedure in which the detection sensitivity is estimated at predetermined light amount level by using the monitored light amount become possible.

As described above, the water quality analyzer according to the first embodiment adjusts the distance D by separating the intersection P1 between the optical axis A1 of the excitation light irradiating optical system 10 and the optical axis A2 of the fluorescence detecting optical system 20 and the intersection P2 between the optical axis B1 of the scattered light irradiating optical system 30 and the optical axis B2 of the scattered light detecting optical system 40 in the sample cell 5. Thereby, the fluorescence detector 21 can detect the fluorescence L2 with high accuracy while suppressing the influence of the transmitted light L3' when measuring the sample water and the scattered light detector 41 can detect the scattered light L4 with high accuracy while suppressing the influence of the transmitted light L1'. In addition, when monitoring the light amount of the excitation light source 11, the light amount can be monitored for the light source 11 by the scattered light detecting optical system 40 without installing a dedicated light amount detector because the scattered light detector 41 can detect the light amount of the transmitted light L1'. When monitoring the light amount of the light source for scattered light detection 31, the light amount can be monitored for the light source 31 by the fluorescence detecting optical system 20 without installing a dedicated light amount detector because the fluorescence detector 21 can detect the light amount of the transmitted light L3'. Thus, water quality analysis can be done stably considering decrease in the light amount of the excitation light source 11 and the light source for scattered light detection 31.

Here, the quality analyzer is applicable to sample water such as drinking water, sewage, environmental water such as sea water, river water and lake water, and waste water and irradiates a specific component in the sample water with excitation light, detects the fluorescence emitted from the specific component and measures the specific component. Excitation light is influenced by scattering and absorption by turbid material and fluorescence intensity of a specific component fluctuates when the concentration of the turbid material contained in the sample water increases. Therefore, the turbidity is measured, and the intensity of fluorescence corrected, in order to measure fluorescence intensity of a specific material with high accuracy.

However, the excitation light has a wavelength band different from that of the light for scattered light detection used to measure the turbidity. Because each sample water has different light absorption characteristic for these two wavelength bands, accurate fluorescence measurement may not be ensured for a specific component in sample water when fluorescence is corrected based on turbidity only. Namely, fluorescence cannot be corrected accurately only by turbidity correction because different types of turbid materials have different excitation light and fluorescence characteristics even if their concentrations are the same. Therefore, the absorbance of sample water is measured based on the fluorescence intensity, the absorption degree of the sample water is detected at the wavelengths of the excitation light and the irradiation light for turbidity measurement, and the fluorescence intensity for the specific component is corrected.

Furthermore, the fluorescence emitted from the specific component in sample water also decreases due to the absorption by the sample water. The wavelength of fluorescence is generally different from those of the excitation light and the irradiation light used for turbidity measurement. To detect the absorbance characteristic at the fluorescence wavelength, it is required to detect absorbance at the fluorescence wavelength in addition to those at the wavelengths of the excitation light and the irradiation light for turbidity measurement. Therefore, there is a need to install a fluorescence light source for irradiating the sample water, a detector for detecting the light source light, and the like, and it makes water quality analyzer configuration complicated.

As seen from above, to measure fluorescence intensity of a specific component accurately, the fluorescence intensity of the specific component is needed to be corrected considering turbidity of sample water and influence depending on a type of turbid material. Although it is known as a conventional correction method in which a specific component is measured by correcting the absorbance at the specific wavelength by the absorbances of the sample water at two wavelengths and suppressing the influences of turbidity of sample water and turbid material, but that method cannot detect any fluorescent component because the water quality analyzer used does not have fluorescence detecting function. A method in which the influence caused by turbid material can be suppressed by correcting the fluorescence intensity of a specific component by using Raman scattered light of sample water is known, but that method cannot measure the turbidity.

Therefore, the water quality analyzer according to the second embodiment has both fluorescence detecting function and turbidity detecting function and it also detect the two types of transmitted lights, the excitation light passed through sample water and irradiation light for turbidity measurement passed through sample water by a transmitted light detecting optical system. The absorbance characteristics at the excitation light wavelength and the irradiation lights wavelength are detected from the transmitted excitation light passed through sample water and the transmitted irradiation light for turbidity measurement passed through sample water, respectively, and the fluorescence intensity is corrected by estimating the absorbance characteristic at the fluorescence wavelength from these characteristics. Thereby, the fluorescence emitted from a specific component in sample water can be measured accurately without increasing the number of wavelength of the light to be irradiated or detected.

The water quality analyzer according to the second embodiment is described in detail below. In the second embodiment, transmitted lights which are light source light for excitation and light source light for scattered light detection passed through a sample cell are detected by a transmitted light detecting optical system. And the absorbances of sample water at the wavelengths of the light source lights for excitation and for scattered light detection are calculated from the transmitted light intensities and the absorbance at the fluorescence wavelength is predicted in a predictor.

Figure 4:
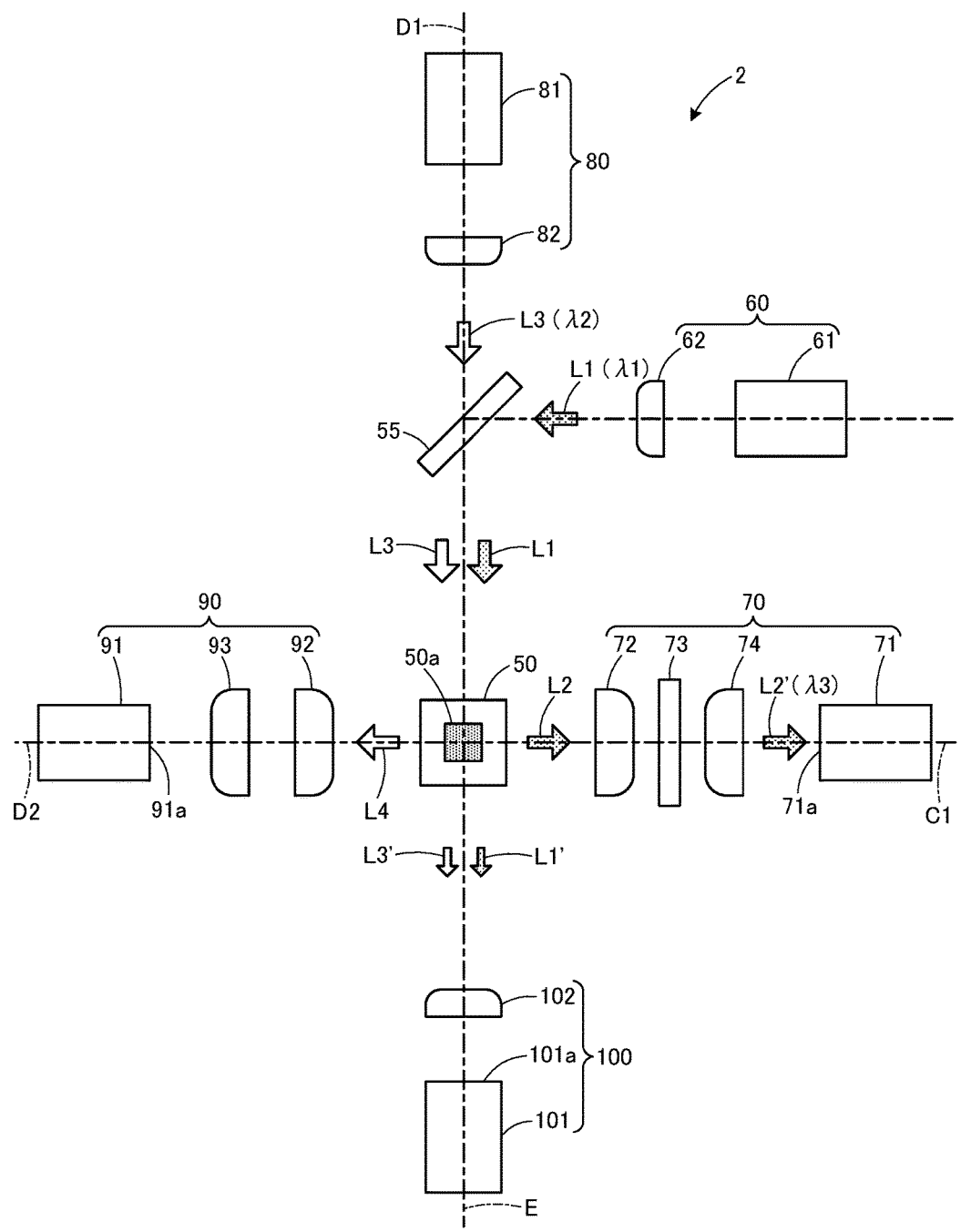
FIG. 4 shows a schematic block diagram of the water quality analyzer according to the second embodiment.
Figure 5:
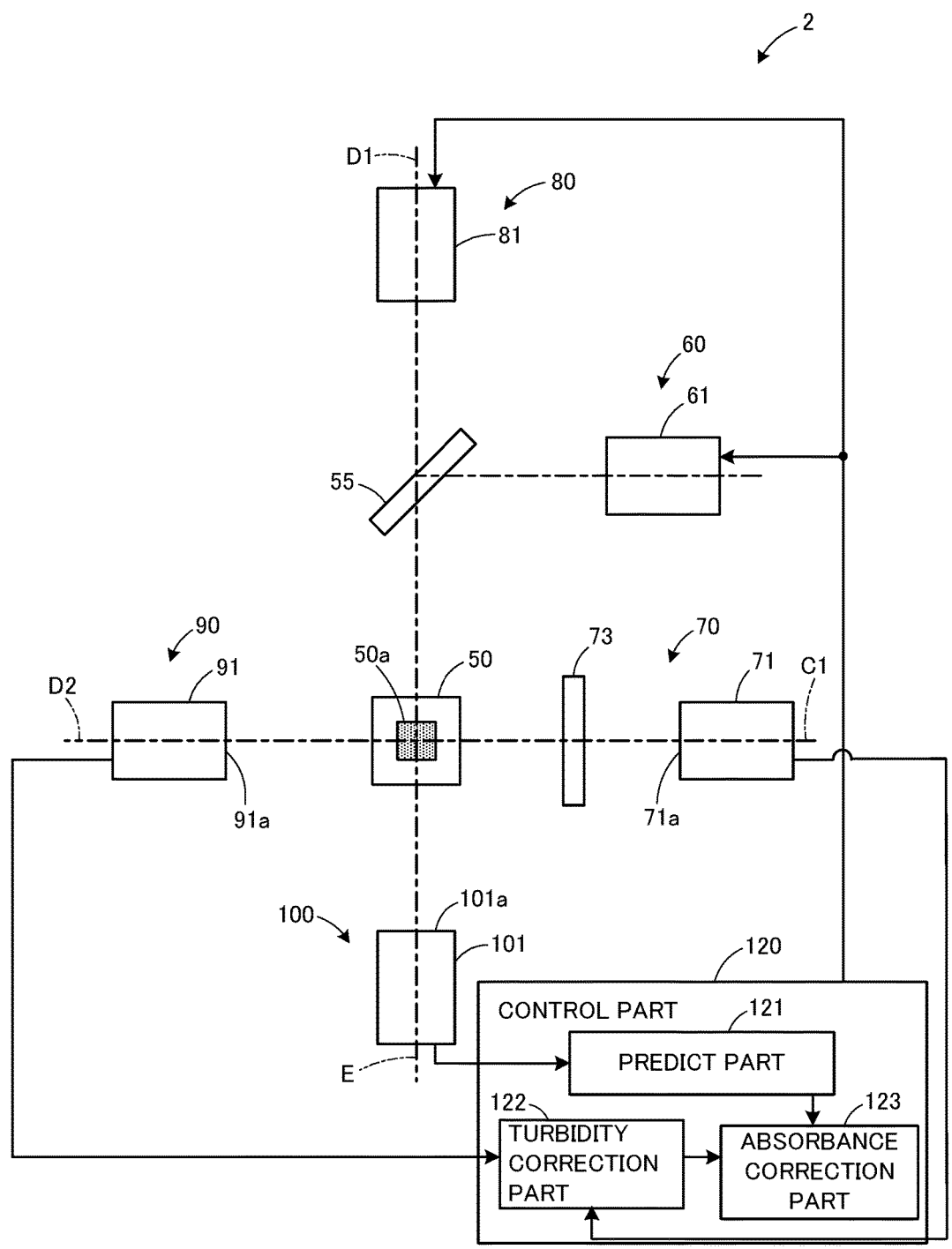
FIG. 5 shows a block diagram showing the configuration of the control part according to the second embodiment.

FIG. 4 is a schematic block diagram of the water quality analyzer according to the second embodiment. FIG. 5 is a block diagram showing the configuration of the control part according to the second embodiment. The water quality analyzer 2 comprises a transmitted detecting optical system 100, a fluorescence detecting optical system 70, a scattered light irradiating optical system for turbidity detection 80, and a scattered light detecting optical system 90 in the four directions around a sample cell 50. The fluorescence detecting optical system 70 and the scattered light detecting optical system 90 are arranged so as to be opposed to each other across the sample cell 50, and the scattered light irradiating optical system 80 and the transmitted light detecting optical system 100 are arranged so as to be opposed to each other across the sample cell 50. A half mirror 55 (an optical member) is provided between the scattered light irradiating optical system 80 and the sample cell 50 and the excitation light irradiating optical system 60 is arranged to the right side of the optical member 55. The optical member 55 is arranged in the position where the light source light for excitation L1 and the light source light for scattered light detection L3, both are described later, are guided to the sample cell 50. The optical member 55 and the transmitted light detecting optical system 100 are opposed to each other across the sample cell 50.

The excitation light irradiation optical system 60 has an excitation light source 61 and a collimator lens 62 arranged between the light source 61 and the optical member 55. The fluorescence detecting optical system 70 has a fluorescence detector 71, a condensing lens 72, an optical filter 73, and a condensing lens 74 arranged between the fluorescence detector 71 and the sample cell 50. The condensing lenses 72, 74 are symmetrically arranged to the optical filter 73. The scattered light irradiating optical system 80 has a light source for scattered light detection 81 and a collimator lens 82 arranged between the light source 81 and the optical member 55. The scattered light detecting optical system 90 has a scattered light detector 91 and condensing lenses 92, 93 arranged between the scattered light detector 91 and the sample cell 50. The transmitted light detecting optical system 100 has a condensing lens 102 arranged between the transmitted light detector 101 and the sample cell 50.

The sample cell 50 is formed into a rectangular cylindrical shape having the sample water channel 50a at the center and extends perpendicular to the optical axis E of the transmitted light detecting optical system 100, the optical axis C1 of the fluorescence detecting optical system 70, the optical axis D1 of the scattered light irradiating optical system 80, and the optical axis D2 of the scattered light detecting optical system 90. Sample water to be measured is made to flow through the sample water channel 50a. As the sample cell 50, a flow cell made of a transparent material such as quartz glass is used, but a rectangular cell made of quartz glass can be also used.

As the excitation light source 61, a light emitting diode, laser diode, and the like, which can emit light having a specific wavelength $\lambda 1$, can be used. As the light source for scattered light detection 81, light emitting diode, laser diode, and the like, which can emit light having a specific wavelength $\lambda 2$, can be used. The wavelength $\lambda 1$ of the light source light for excitation L1 is, e.g., from 250 to 350 nm, and the wavelength of the light source light for scattered light detection L3 is, e.g., from 600 to 900 nm.

As the scattered light detector 91, a silicon photodiode and the like, for which the light source light for scattered light detection L3 having wavelength $\lambda 2$ is within its detection range can be used. As the fluorescence detector 71, a photomultiplier tube, and the like can be used and thereby, weak specific fluorescence having wavelength $\lambda 3$ selectively passed through an optical filter 73 can be detected. As the optical filter 73, but not limited to it, a bandpass filter, and the like can be used which selectively pass only the fluorescence having wavelength $\lambda 3$ emitted by a component to be detected. Thus, light having a wavelength other than $\lambda 3$ is cut by the filter. As the specific wavelength $\lambda 3$, from the viewpoint of increasing detection rate of the fluorescence detector 71, the peak wavelength of fluorescence may be selected. The wavelength $\lambda 3$ is, e.g., from the wavelength $\lambda 1$ to the wavelength $\lambda 2$. Thereby, absorbance at the wavelength $\lambda 3$ can be measured with high accuracy in a predict part described later. As the transmitted light detector 101, a silicon photodiode, and the like for which the light having the wavelength $\lambda 1$ of the light source light for excitation L1 and the light having the wavelength $\lambda 2$ of the light source light for scattered light detection L3 are within its detection range can be used. As the optical member 55, a half mirror, a beam splitter, and the like can be used.

In these configurations, the excitation light source 61 and the light source for scattered light detection 81 are alternately lighten when measuring sample water. Real sample is made to flow through the sample water channel 50a of the sample cell 50. The excitation light source 61 emits the light source light for excitation L1 having wavelength λ1 and the light source light L1 passes through the collimating lens 62 and becomes nearly parallel beams (collimator light), then be reflected by the optical member 55 and is made to irradiate the sample water in the sample cell 50. The component to be detected in the sample water is excited by the light source light L1 and emits the fluorescence L2. The fluorescence L2 is condensed by the condensing lens 72 and reaches the optical filter 73, after selecting the light L2' having the specific wavelength λ3 by the optical filter 73, is condensed by the condensing lens 74, and reaches the light receiving surface 71a of the fluorescence detector 71. A part of the light source light L1 advances straightly in the sample cell 50 and passes through the sample cell 50, and then is condensed as the transmitted light L1' by the condensing lens 102 and reaches the light receiving surface 101a of the transmitted light detector 101.

The light source for scattered light detection 81 emits the light source light for scattered light detection L3 having the wavelength λ2 and the light source light L3 passes through the collimating lens 82 and becomes nearly parallel beam and passes through the optical member 55 and is made to irradiate sample water in the sample cell 50. The light source light L3 is scattered by microparticles, suspending materials in the sample water, and the scattered light L4 is emitted. The scattered light L4 is condensed by the condensing lenses 92, 93 and reaches the light receiving surface 91a of the scattered light detector 91. A part of the light source light L3 advances straightly in the sample cell 50 and passes through the sample cell 50, and then is condensed as the transmitted light L3' by the condensing lens 102 and reaches the light receiving surface 101a of the transmitted light detector.

As seen from above, in the water quality analyzer 2, when measuring sample water, the fluorescence intensity is measured by irradiating the sample cell 50 with the light source light for excitation L1 having the wavelength λ1 from the excitation light source 61 and detecting the fluorescence L2 having the wavelength λ3 emitted from the specific component in sample water excited by irradiation of the light source light L1 by the fluorescence detector 71. At the same time, turbidity is measured by irradiating the sample cell 50 with the light source light for scattered light detection L3 having the wavelength λ2 by the light source for scattered light detection 81 and detecting the scattered light L4 scattered by microparticles in the sample water irradiated with the light source light L3 by the scattered light detector 91. The fluorescence intensity of the specific component in the sample water to be detected can be measured under the consideration of the influence of the turbidity because fluorescence is detected while detecting scattered light.

The light propagated in the direction of the light source light for excitation L1 which is reflected by the optical member 55 is orthogonal to the optical axis C1 of the fluorescence detecting optical system 70. Therefore, the fluorescence detector 71 can detect the fluorescence L2' emitted from the specific component in sample water while suppressing the introduction of the transmitted light L1' into the fluorescence detector 71. The optical axis D1 of the scattered light irradiating optical system 80 is orthogonal to the optical axis D2 of the scattered light detecting optical system 90. Therefore, the scattered light detector 91 can detect the scattered light L4 emitted from microparticles in sample water while suppressing the introduction of the transmitted light L3' into the scattered light detector 91.

In the water quality analyzer 2, the transmitted light detecting optical system 100 is arranged so as to be opposed to the optical member 55 across the sample cell 50 and to guide the light source light for excitation L1 and the light source light for scattered light detection L3 to the sample cell 50. Therefore, when measuring sample water, the light source light for excitation L1 having the wavelength λ1 irradiated from the excitation light source 61 is reflected by the optical member 55 and is introduced into the sample cell 50, and the transmitted light detector 101 can detect the transmitted light L1' passed through the sample cell 50. The light source light for scattered light detection L3 having the wavelength λ2 irradiated from the light source for scattered light detection 81 passes through the optical member 55 and is introduced into the sample cell 50, and the fluorescence detector 71 can detect the transmitted light L3' passed through the sample cell 50. The absorbance of a real sample can be obtained by calculating the transmitted light ratio in the case where a real sample and pure water are made to flow through the sample cell 50 in the predict part 121 described later (see FIG. 5) from the intensities of thus-detected transmitted lights L1', L3'.

As shown in FIG. 5, the water quality analyzer 2 comprises a control part 120 which controls each part integrally. The control part 120 put on and put out the excitation light source 61 and the light source for scattered light detection 81 repeatedly by switching a fluorescence detection mode and a turbidity detection mode described later. The control part 120 consists of processors, memories, and the like which execute various processing. The memory consists of one or several storage media such as ROM (Read Only Memory) and RAM (Random Access Memory) depending on its use. The control part 120 has a predict part 121, a turbidity correction part 122, and an absorbance correction part 123. The control part 120 may consist of a control circuit, a control device, a controller, and the like.

The predict part 121 calculates absorbance of sample water for the light source light L1 having the wavelength λ1 from the transmitted light L1' detected by the transmitted light detector 101 and it also calculates the absorbance of the sample water for the light source light for scattered light detection L3 having the wavelength λ2 from the transmitted light L3'. The absorbance of the sample water for the fluorescence with wavelength λ3 is predicted from the absorbances of the sample water at the wavelength λ1 and the wavelength λ2. The predict part 121 may be consisted of a predict circuit, a predict device, a predictor. The turbidity correction part 122 performs turbidity-based fluorescence intensity correction in which the fluorescence intensity of the sample water detected by the fluorescence detector 71 is corrected by using the turbidity measured based on the scattered light L4 having the wavelength λ2 detected by the scattered light detector 91. The turbidity correction part 122 may be consisted of a turbidity correction circuit, a turbidity correction device, a turbidity corrector, and the like. The absorbance correction part 123 calculates an absorbance-corrected fluorescence intensity by correcting the fluorescence intensity corrected for turbidity in the turbidity correction part 122 by using the absorbance of the sample water at the wavelength λ1 calculated by the predict part 121 and the predicted absorbance at the wavelength λ3. The absorbance correction part 123 may consist of an absorbance correction circuit, an absorbance correction device, an absorbance corrector, and the like. As described above, in the water quality analyzer 2, the absorbance at the wavelength $\lambda 3$ is predicted from the absorbances of the sample water at the wavelength $\lambda 1$ and the wavelength $\lambda 2$. This can make the configuration of the water quality analyzer 2 simple because it is not required to install a light source for irradiating light having the wavelength $\lambda 3$ to measure the absorbance of the sample water at the wavelength $\lambda 3$ and to correct the fluorescence intensity by using actual measurements.

Figure 6A:
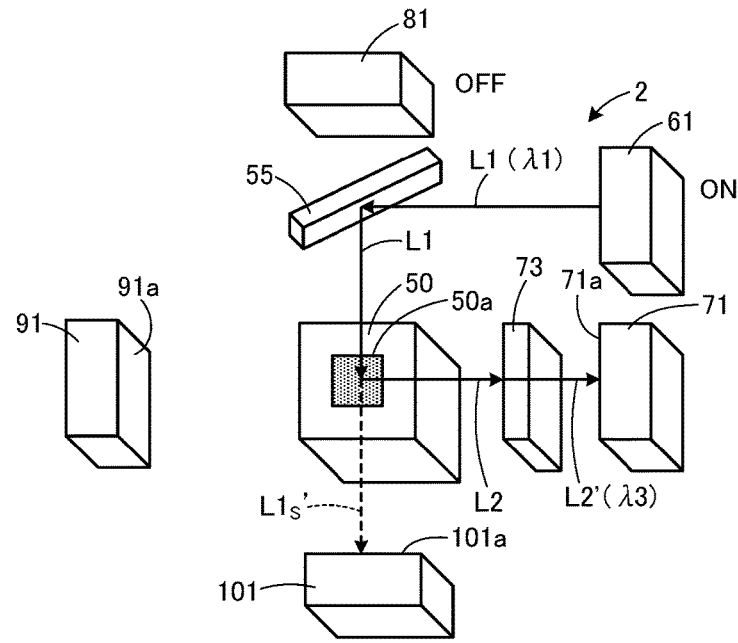
FIGS. 6A and 6B show explanation drawings for describing the measuring operation in normal measuring mode of the water quality analyzer according to the second embodiment.
Figure 6B:
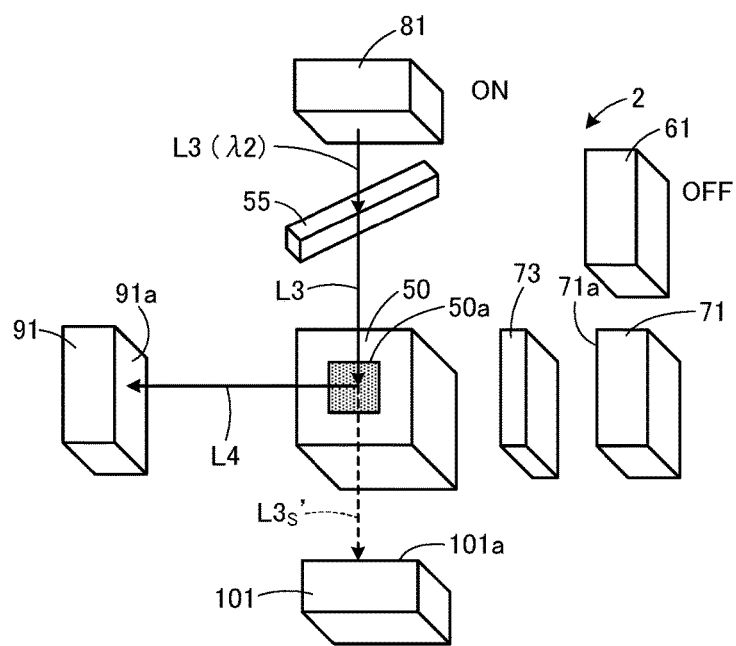
Figure 7A:
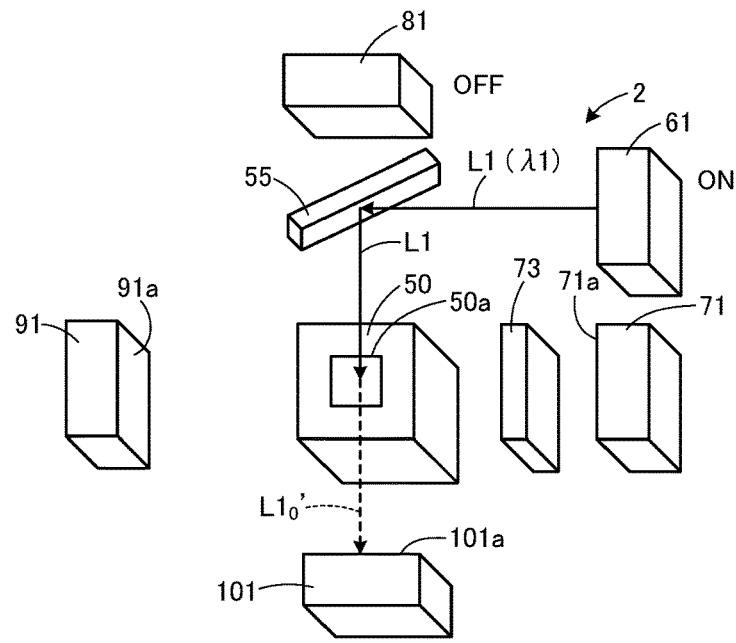
FIGS. 7A and 7B show explanation drawings for describing the measuring operation in pure water measuring mode of the water analyzer according to the second embodiment.
Figure 7B:
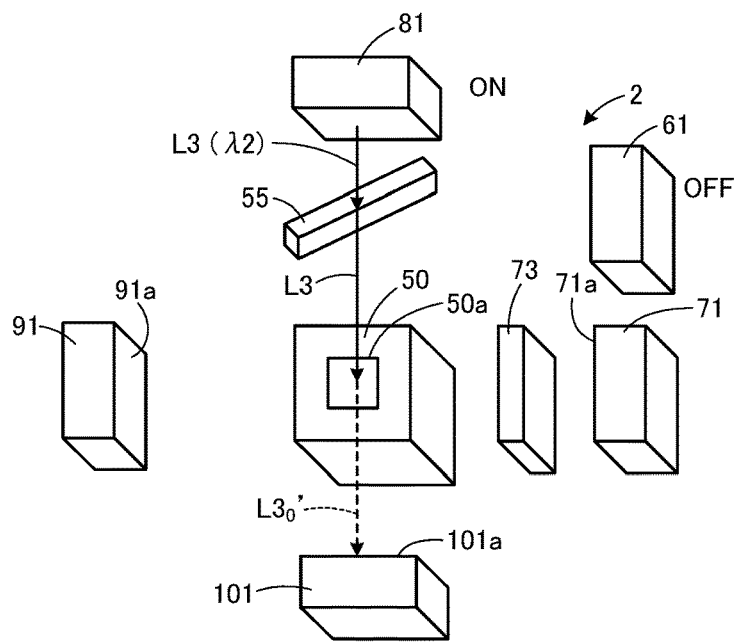
Figure 8:
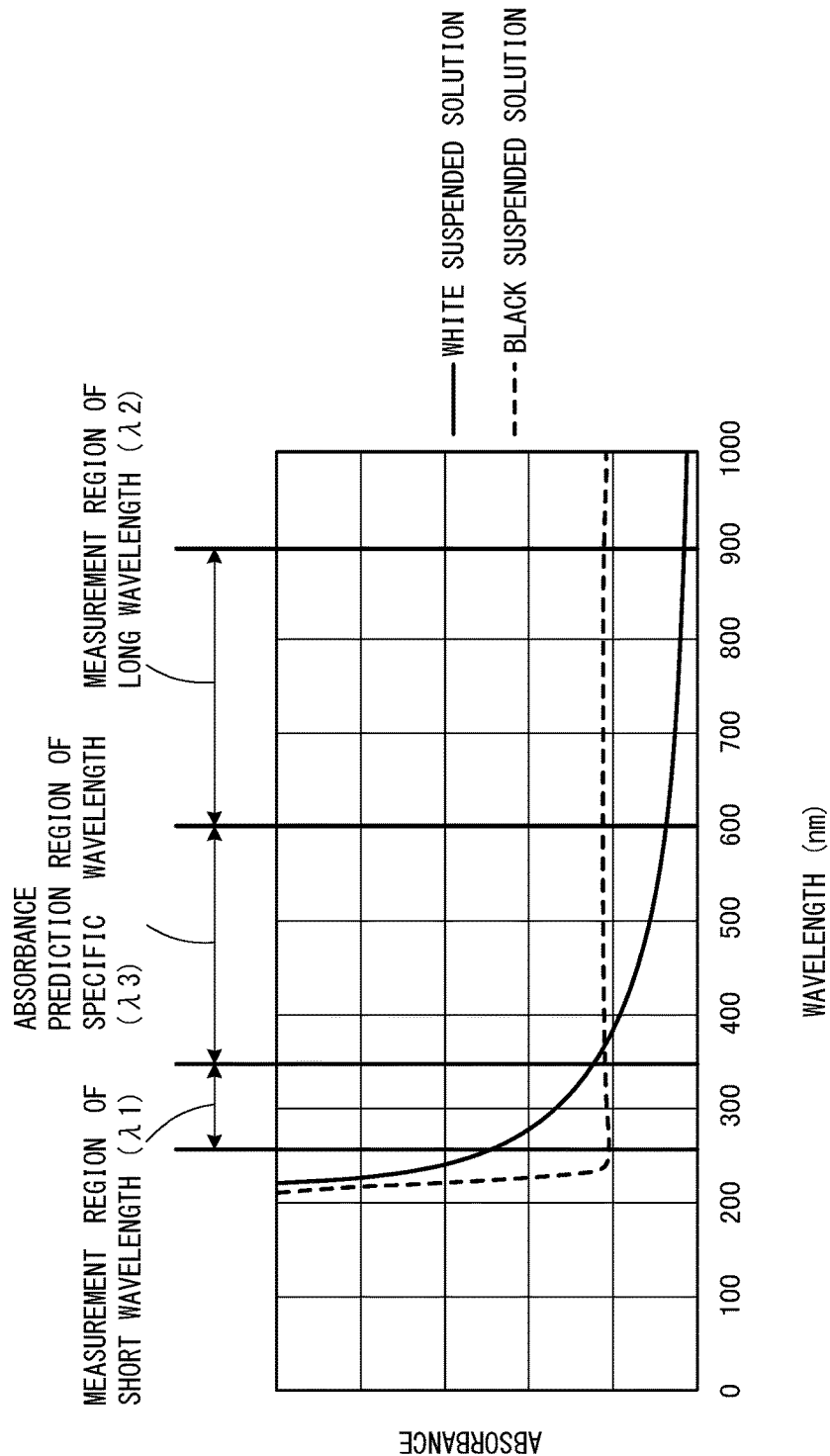
FIG. 8 shows a drawing for illustrating an example of measuring the absorbance of sample water containing suspending materials.

Next, a measuring operation of sample water by the water quality analyzer 2 according to the second embodiment will be described with reference FIGS. 6A and 6B and Table 2. FIGS. 6A and 6B are explanation drawings for describing the measuring operation in normal measuring mode of the water quality analyzer according to the second embodiment. FIG. 6A is an explanation drawing presenting measurement operations relating to fluorescence intensity of a real sample and transmitted light of the light source light of an excitation light source according to the second embodiment. FIG. 6B is an explanation drawing presenting a measurement operation relating to scattered light intensity of a real sample and the transmitted light of the light source light for scattered light detection according to the second embodiment. FIGS. 7A and 7B are explanation drawings presenting a measurement operation of the water quality analyzer according to the second embodiment in pure water measuring mode. FIG. 7A is an explanation drawing presenting a measurement operation relating to transmitted light of the light source light of the excitation light source for pure water according to the second embodiment. FIG. 7B is an explanation drawing presenting a measurement operation relating to transmitted light of the light source light for scattered light detection for pure water according to the second embodiment. FIG. 8 is a drawing for illustrating an example of measuring the absorbance of sample water containing suspending materials. In FIG. 8, the abscissa represents wavelength and the ordinate represents absorbance, respectively. In Table 2, for each of normal measurement mode and pure water measurement mode, both fluorescence detection mode and turbidity detection mode are described and switching between normal measurement mode and pure water measurement mode as well as between fluorescence detection mode and turbidity detection mode is performed by the control part 120 (see FIG. 5).

[Table 2]

As shown in FIGS. 6A and 6B, when measuring real samples, the normal measurement mode in Table 2 is selected, and real samples are made to flow through the sample water channel 50a of the sample cell 50. As shown in FIG. 6A, when measuring the intensity of the fluorescence L2' from the specific component in the real sample to be detected and the transmitted light L1$s$' that is the light source light L1 for excitation passed through the sample cell 50, the fluorescence detection mode in the normal measurement mode is selected and the intensities of the fluorescence L2 and the intensity of the transmitted light L1$s$' are measured. The excitation light source 61 is set to ON state and the light source for scattered light detection 81 is set to OFF. The excitation light source 61 emits the light source light L1 for excitation having the wavelength $\lambda 1$ and the light source light L1 is reflected by the optical member 55 to irradiate the real sample in the sample cell 50. A component to be detected in the real sample is excited by the light source light L1 and emits the fluorescence L2 having the peak wavelength shifted on the side of longer wavelength than that of the light source light L1 for excitation having the wavelength $\lambda 1$, and the fluorescence L2 reaches the light receiving surface 71a of the fluorescence detector 71 after extracting the light L2' with the specific wavelength $\lambda 3$ by the optical filter 73. A part of the light source light L1 advances straightly in the sample cell 50 and passes through the sample cell 5, and then reaches the light receiving surface 101a of the transmitted light detector 101 as the transmitted light L1$s$'.

As shown in 6B, when measuring the intensity of the scattered light L4 of the sample water and the transmitted light L3$s$' that is the light source light for scattered light detection L3 passed through the sample cell 50, the turbidity detection mode in the normal measurement mode in Table 2 is selected and the intensities of the scattered light L4 and the transmitted light L3$s$' are measured. The excitation light source 61 is set to OFF state and the light source for scattered light detection 81 is set to ON. The light source for scattered light detection 81 emits the light source light for scattered light detection L3 having the wavelength $\lambda 2$ and the light source light L3 passes through the optical member 55 and is made to irradiate the real sample in the sample cell 50. The light source light L3 is scattered by microparticles in the real sample and the scattered light L4 reaches the light receiving surface 91a of the scattered light detector 91. A part of the light source light L3 advances straightly in the sample cell 50 and passes through the sample cell 50, and then reaches the light receiving surface 101a of the transmitted light detector 101 as the transmitted light L3$s$'.

As described above, in the fluorescence detection mode, the fluorescence detector 71 detects the fluorescence component L2' having the wavelength $\lambda 3$ of the real sample and the transmitted light detector 101 detects the transmitted light L1$s$'. In the turbidity measurement mode, the scattered light detector 91 detects the scattered light L4 of the real sample and the transmitted light detector 101 detects the transmitted L3$s$'. Two types of light, the transmitted light L1'$s$ of the light source light for excitation L1 and the transmitted light L3$s$' of the light source light for scattered light detection L3, reach the transmitted light detector 101. The water quality analyzer 2 repeat to light on and off the excitation light source 61 and the light source for scattered light detection 81 alternately by switching detection mode between the fluorescence detection mode and the turbidity detection mode by the control part 120 (see FIG. 5). In this way, the detection signal of the transmitted light L1$s$' detected by the transmitted light detector 101 is separated from that of the detection signal of the transmitted light L3$s$'.

As shown in FIGS. 7A and 7B, when measuring pure water, the pure water measuring mode in Table 2 is selected and pure water is made to flow the sample water channel 50a of the sample cell 50. As FIG. 7A shows, when measuring the transmitted light L1$o$' that is the light source light for excitation L1 passed through the pure water in the sample cell 50, the fluorescence detection mode in the pure water measurement mode is selected, and the transmitted light detector 101 detects the intensity of the transmitted light L1$o$'. The excitation light source 61 is set to ON state and the light source for scattered light detection 81 is set to OFF state. The light source light L1 having the wavelength $\lambda 1$ emitted from the excitation light source 61 is reflected by the optical member 55 and is made to irradiate the pure water in the sample cell 50. The light source light L1 passes through the sample cell 5 and reaches the light receiving surface 101a of the transmitted light detector 101 as the transmitted light L1$o$', and the transmitted light L1$o$' is detected.

As shown in FIG. 7B, when measuring the transmitted light L3$o$' that is the light source for scattered light detection 81 passed through the pure water in the sample cell 50, the turbidity detection mode in the pure water measurement mode is selected and the transmitted light detector 101 detects the intensity of the transmitted light L3o'. The excitation light source 61 is set to OFF state and the light source for scattered light detection 81 is set to ON state. The light source light L3 having the wavelength λ2 emitted from the light source for scattered light detection 81 passes through the optical member 55 and is made to irradiate the pure water in the sample cell 50. The light source light L3 passes thorough the sample cell 50 and reaches the light receiving surface 101*a* of the transmitted light detector 101 as the transmitted light L3o', and the transmitted light L3o' is detected.

In the predict part 121 (see FIG. 5), the absorbance representing the absorption degree of the sample water is calculated by using the transmitted light L1s', L1o' that is the light source light for excitation L1 detected by the transmitted detector 101 and L3s', L3o' which are the light source lights for scattered light detection L3. The absorbance of real sample (ABS) is expressed by the formula (1):

$$ABS=-\log(Is/Io) \tag{1}$$

wherein, the transmitted light intensity of the pure water not contain turbid materials (as sample water) is Io and the transmitted light intensities of the real sample containing turbid materials (as sample water) is Is.

In the predict part 121, by using the formula (1), the absorbance $A_{\lambda 1}$ of real sample is calculated for the light source light for excitation L1 having the wavelength λ1 from the transmitted light L1s' detected in the fluorescence detection mode of the normal measurement mode and the transmitted light L1o' detected in the fluorescence detection mode of the pure water measurement mode. The absorbance $A_{\lambda 2}$ of real sample is calculated for the light source light for scattered light detection L3 having the wavelength λ2 from the transmitted light L3s' detected in the turbidity detection mode in the normal measurement mode and the transmitted light L3o' detected in the turbidity detection mode of the pure water measurement mode. In the water quality analyzer 2, the pure water measurement mode is selected in the control part 120 (see FIG. 5) and the transmitted light L1o' that is the light source light for excitation L1 passed through pure water and the transmitted light L3o' that is the light source light for scattered light detection L3 passed through pure water are previously or periodically measured. This make it possible to calculate the absorbances $A_{\lambda 1}, A_{\lambda 2}$ of real samples at the wavelengths of λ1, λ2 when detecting the intensities of the transmitted light L1s', L3's for real samples in the normal measurement mode.

Here, types of turbid materials and absorbance characteristics of sample water will be explained. Even if concentration of turbid material in a sample water, i.e. the turbidity is the same, different turbid materials have different characteristics of excitation light and fluorescence. In FIG. 8, the solid line and the broken line indicate the absorption spectrums of a white suspended solution and a black suspended solution, respectively. These two suspended solutions show the same turbidity in scattered light measuring but their absorption spectrums are markedly different since they differ in the kind of turbid materials. Sample water containing white turbid materials have a larger absorbance on a side of a shorter wavelength and a smaller absorbance on a side of a longer wavelength. On the other hand, sample water containing black turbid materials have the same level of absorbance from a short wavelength to a long wavelength. Because the larger the absorbance, the larger a water absorbs light at the given wavelength, the fluorescence intensity detected by the fluorescence detector 71 becomes smaller even if the concentrations of components to be detected in the sample water are the same.

Absolute values of the absorbance on a side of a shorter wavelength and the absorbance on a side of a longer wavelength and the ratio of the absolute values differs widely according to the type of turbid materials contained in sample water. This makes it possible to predict the absorbance at a specific wavelength, i.e. at fluorescence wavelength between a shorter and a longer wavelength, from the absolute values of the absorbances on sides of a shorter and a longer wavelength and the ratio of them. For prediction of the absorbance at the specific wavelength, linear approximation technique, and the like can be used.

When the wavelength λ1 of the light source light for excitation L1 is set on a side of a short wavelength, in ultraviolet region, for example, a range from 250 to 350 nm, the fluorescence of organic materials and/or oil, and the like to be detected in a real sample appears, for example, around from 350 to 500 nm as the peak wavelength. Thus, the fluorescence having the wavelength λ3 emitted by the specific component in the sample water appears. On the other hand, as the wavelength λ2 of the light source light for scattered light detection L3 used in turbidity measurement, a visible light or a near infrared light having a long wavelength, for example, a wavelength ranged from 600 to 900 nm is used.

In the predict part 121, the absorbance $A_{\lambda 1}$ of real sample for the light source light for excitation L1 having the wavelength λ1 is calculated from the measured transmitted lights L1s', L1o', and the absorbance $A_{\lambda 2}$ of a real sample for the light source light for scattered light detection L3 having the wavelength λ2 is calculated from the measured transmitted lights L3s', L3o'. In the predict part 121, the absorbance $A_{\lambda 3}$ of the fluorescence at the wavelength λ3 between wavelength λ1 and λ2 is predicted from the absolute values of the absorbance $A_{\lambda 1}$ on sides of a short wavelength λ1 and the absorbance $A_{\lambda 2}$ on sides of a short wavelength λ2 and the ratio of them. The wavelength λ3 is, e.g., the peak wavelength of the fluorescence spectrum.

In the turbidity correction part 122 (see FIG. 5), the turbidity correction of the fluorescence intensity is performed by correcting the intensity of the fluorescence L2' of the sample water detected by the fluorescence detector 71 by using the turbidity measured based on the principle that the intensity of the scattered light L4 having the wavelength λ2 detected by the scattered detector 91 is proportional to the concentration of turbid material. The turbidity correction is performed by using the turbidity correction formula (2). The fluorescence intensity F1 after turbidity correction is represented by formula (2) wherein turbidity is X and the fluorescence intensity detected by the fluorescence detector 71 is Fo.

$$F_1=(aX^2+bX+c)\times F_0 \tag{2}$$

a, b, c: constant

The absorbance $A_{\lambda 1}$ at the wavelength λ1 calculated by the predict part 121 and the absorbance $A_{\lambda 3}$ of real sample at the predicted wavelength λ3 as well as the fluorescence intensity F1 corrected for turbidity by the turbidity correction part 122 are outputted to the absorbance correction part 123 (see FIG. 5). In the absorbance correction part 123, the absorbance-corrected fluorescence intensity is calculated by correcting the fluorescence intensity F1 corrected for turbidity by use of the absorbance $A_{\lambda 1}$ of real sample at the wavelength λ1 and the absorbance $A_{\lambda 3}$ at the predicted wavelength λ3. The absorbance correction is performed by using formula (3). The fluorescence intensity F2 after absorbance correction is represented by formula (3)

$$F_2 = k \times F_1 \times \exp((A_{\lambda 1} + A_{\lambda 3})/2) \quad (3)$$

k: constant

As described above, it is possible to consider the effects of absorbance characteristics of excitation light and fluorescence of real samples by predicting the absorbance $A_{\lambda 3}$ at the wavelength $\lambda 3$ from the absorbances $A_{\lambda 1}$, $A_{\lambda 2}$ of real samples at the wavelength $\lambda 1$ and $\lambda 2$ that is calculated from the measured transmitted lights L1$s'$, L1$o'$ and L3$o'$, L2$o'$. This can make it possible to measure the fluorescence intensity of the component to be detected accurately regardless of the kind of turbid material. It also possible to make the configuration of the water quality analyzer simple because a light source for irradiating fluorescence required to detect the absorbance characteristic of the fluorescence having the wavelength $\lambda 3$, and the like is not necessary.

As described above, the water quality analyzer 2 according to the second embodiment calculates the absorbances $A_{\lambda 1}$, $A_{\lambda 2}$ of the sample water at the first wavelength $\lambda 1$ and the second wavelength $\lambda 2$ by using the transmitted light L1' of the light source light for excitation L1 at the first wavelength $\lambda 1$ and the transmitted light L3' of the light source light for scattered light detection L3 at the second wavelength $\lambda 2$. The absorbance $A_{\lambda 3}$ of the fluorescence having the third wavelength $\lambda 3$ is predicted by using these absorbances $A_{\lambda 1}$, $A_{\lambda 2}$, and the absorbance $A_{\lambda 3}$ of the fluorescence having the third wavelength $\lambda 3$ is used for correcting the fluorescence intensity of the component to be measured. This makes it possible to measure the fluorescence intensity with high accuracy and it is also possible to make the configuration of the water quality analyzer 2 simple because there is no need to install the light source for irradiating the light having the third wavelength $\lambda 3$, the detector for detecting the transmitted light of this light source light, and the like in the water quality analyzer to correct the fluorescence intensity.

Incidentally, the preset invention is not limited to the first and the second embodiment, it can be performed in various altered embodiments. For the embodiments above, the size and the shape indicated in the attached drawings is not limited to them, they can be changed appropriately provided that the advantage of the invention is provided. In addition, the present invention can be altered and performed provided that the alternation is not deviated from the purpose of the invention.

For example, in the first embodiment, the arrangement of each optical system 10, 20, 30, 40 is not particularly limited provided that the fluorescence detecting optical system 20 is arranged so as to detect the light amount of the scattered light irradiating optical system 30 and the scattered light detecting system 40 is arranged so as to detect the light amount of the excitation light irradiating optical system 10.

In addition, in the first embodiment, the configuration of each optical system 10, 20, 30, 40 is not particularly limited provided that the fluorescence L2 and the transmitted light L3' is introduced into the light receiving surface 21$a$ of the fluorescence detector 21 and the scattered light L4 and the transmitted light L1' is introduced into the light receiving surface 41$a$ of the scattered light detector 41.

Further, in the first embodiment, the excitation light irradiating optical system 10 and the scattered light irradiating optical system 30 are configured to comprise collimate lens 12, 32 but they do not necessarily to comprise collimate lenses 12, 32 when a light source which lenses have been previously integrated and can generate nearly parallel light is used for the light sources 11, 31.

In addition, in the first embodiment, the sample cell 5 is configured to be formed into cylindrical shape but it is not necessary limited to this configuration provided that the fluorescence detector 21 can detect the fluorescence L2 and the transmitted light L3' and the scattered light detector 41 can detect the scattered light L4 and the transmitted L1'.

For example, in the second embodiment, the arrangement of each optical system 60, 70, 80, 90, 100 is not particularly limited provided that transmitted light detector 100 is configured to be able to detect the light amount of the scattered light irradiating optical system 80 and detect the light amount of the excitation light irradiating optical system 60.

Furthermore, in the second embodiment, the configuration of each optical system 60, 70, 80, 90, 100 is not particularly limited provided that the fluorescence L2' is introduced into the light receiving surface 71$a$ of the fluorescence detector 71 and the scattered light L4 is introduced into the light receiving surface 91$a$ of the scattered light detector 91, and the transmitted lights L1', L3' are introduced into the light receiving surface 101$a$ of the transmitted light detector 101.

In addition, in the second embodiment, the excitation light irradiating optical system 60 and the scattered light irradiating optical system 80 are configured to comprise collimate lens 62, 82 but may be not comprise collimate lenses 62, 82 provided that a light source which lenses have been previously integrated in the light sources 61, 81 and the light source which can generate nearly parallel light is used for the light sources 61, 81.

In addition, in the second embodiment, the sample cell 50 is configured to be formed into cylindrical shape, but not limited to this configuration provided that the fluorescence detector 71 can detect the fluorescence L2', the fluorescence detector 41 can detect the fluorescence L4 and the transmitted detector 101 can detect the transmitted lights L1', L3'.

Furthermore, the configuration of the second embodiment in which the absorbance $A_{\lambda 3}$ at the wavelength $\lambda 3$ is predicted from the absorbances $A_{\lambda 1}$, $A_{\lambda 2}$ of the measured wavelength $\lambda 1$, $\lambda 2$ and the fluorescence intensity is corrected based on the predicted absorbances may be applicable to the first embodiment. In this case, the absorbance $A_{\lambda 2}$ at the wavelength $\lambda 2$ is calculated from the transmitted lights L3' having the wavelength $\lambda 2$ of the light source for scattered light detection 31 detected by the fluorescence detector 21 when real sample and pure water are made to flow through the sample cell 5. The absorbance $A_{\lambda 1}$ at the wavelength $\lambda 1$ is calculated from the transmitted lights L1' having the wavelength $\lambda 1$ of the excitation light source 11 detected by the scattered light detector 41. The absorbance $A_{\lambda 3}$ at the wavelength $\lambda 3$ can be predicted from these calculated absorbances.

Characteristic points of the embodiments above will be summarized below. The water quality analyzer of the present invention comprises a excitation light irradiating optical system to irradiate sample water to be measured with light source light for excitation, a fluorescence detecting optical system to detect fluorescence of a specific component in the sample water excited by irradiation of the light source light for excitation, a scattered light irradiating optical system to irradiate the sample water with light source light for scattered light detection, and a scattered light detecting optical system to detect scattered light generated by microparticles in the sample water receiving irradiation of the light source light for scattered light detection, and is characterized in that the fluorescence detecting optical system is arranged so as to detect the light amount of the scattered light irradiating optical system and the scattered light detecting optical system is arranged so as to detect the light amount of the excitation light irradiating optical system.

This configuration makes it possible to measure fluorescence intensity of sample water with high accuracy in consideration of effect of turbidity of sample water because fluorescence is detected by the fluorescence detecting optical system while scattered light is detected by the scattered light detecting optical system when measuring sample water. When monitoring light amount of an excitation light source, it is possible to monitor the light amount of the excitation light source by the scattered light detecting optical system without installing a dedicate light amount detector because the scattered light detecting optical system can also detect the light amount of the excitation light source. When monitoring light amount of the light source for scattered light detection, it is possible to monitor the light amount of the light source for scattered light detection by the fluorescence detecting optical system without installing a dedicate light amount detector because the fluorescence detecting optical system can also detect the light amount of the excitation light source. This allows stable water quality analysis in consideration of the reduction of light amounts of the light sources for excitation and scattered light detection.

In the water quality analyzer of the present invention, the excitation light irradiating optical system and the scattered light detecting optical system are arranged so as to be opposed to each other across a sample water passing container, and the scattered light irradiating optical system and the fluorescence detecting optical system are arranged so as to be opposed to each other across the sample water passing container. This configuration makes it possible to detect the light amount of transmitted light that is the light source light for excitation passed through the sample water passing container because the excitation light irradiating optical system and the scattered light detecting optical system are arranged to face each other. The scattered light irradiating optical system and the fluorescence detecting optical system are arranged to face o each other, so the light amount of transmitted light that is the light source light for scattered light detection passed through the sample water passing container can be detected. Thereby, it is possible to implement light amount monitoring for each light source.

In the water quality analyzer of the present invention, at the center of the sample water passing container, an optical axis of the excitation light irradiating system and an optical axis of the fluorescence detecting optical system 20 are arranged so as to cross perpendicularly each other and an optical axis of the scattered light irradiating optical system and an optical axis of the scattered light detecting optical system are arranged so as to cross perpendicularly each other. This configuration makes it possible to detect fluorescence from a specific component in sample water by the fluorescence detecting optical system while suppressing effect of transmitted light that is the light source light for excitation passed through the sample water passing container. It is possible to detect the scattered light emitted from microparticles in the sample water by the scattered light detecting optical system while suppressing effect of transmitted light that is the light source light for scattered light detection passed through the sample water passing container.

In the water quality analyzer of the present invention, a first intersection point between the optical axis of the excitation light irradiating optical system and the optical axis of the fluorescence detecting optical system and a second intersection point between the optical axis of the scattered light irradiating optical system and the optical axis of the scattered light detecting optical system are mutually separated in the sample water passing container with a distance. This configuration makes it possible to maintain accuracy of detecting function of light source light for excitation while suppressing effect of transmitted light that is the light source light for scattered light detection passed through the sample water passing container in the fluorescence detecting optical system when measuring sample water because the optical axis of the scattered light irradiating optical system and the optical axis of the fluorescence detecting optical system are mutually separated with a distance. Because the optical axis of the excitation light irradiating optical system and the optical axis of the scattered light detecting optical system are separated mutually with a distance, it is possible to maintain accuracy of detecting function of the light source light for scattered light detection while suppressing effect of transmitted light that is the light source light for scattered light detection passed through the sample water passing container in the scattered light detecting optical system when measuring samples.

In the water quality analyzer of the present invention, the distance between the first intersection point and the second intersection point is, e.g., more than 0 mm and equal to or less than 10 mm. This configuration makes it possible to suppress effect of lights amounts of the transmitted lights that are the light source lights for scattered light detection and excitation passed through the sample water passing container and introduced into the fluorescence detecting optical system and the scattered light detecting optical system when measuring samples.

The water quality analyzer of the present invention comprise a predict part in which an absorbance of sample water at a first wavelength of the light source light is calculated from the first transmitted light that is the light source light for excitation passed through sample water and an absorbance of sample water at a second wavelength of the light source light is calculated from the second transmitted light that is the light source light for scattered light detection passed through the sample water, and then an absorbance of sample water at a third wavelength of the light source light is predicted from the absorbances of sample water at the first and the second wavelengths. By this configuration, the absorbances of sample water at the first and the second wavelengths are calculated from the transmitted lights of the light sources for excitation at the first wavelength and scattered light detection at the second wavelength. By using these absorbances, the absorbance at the third wavelength fluorescence is predicted and the absorbance at the third wavelength fluorescence is used for correction of fluorescence intensity of the component to be measured. Thereby, it is possible to measure the fluorescence intensity with high accuracy and it also possible to make configuration of the water quality analyzer simple because it is not required to measure the absorbance of sample water at the third wavelength by installing a light source for irradiating the light having the third wavelength for fluorescence intensity correction and a detector for detecting the transmitted light of this light source light in the water analyzer.

In the water quality analyzer of the present invention, the absorbance of sample water at the third wavelength is predicted from absolute values of the absorbances of sample water at the first and the second wavelengths and a ratio of the absolute values. By this configuration, the absorbance at the third wavelength can be predicted with high accuracy depending on a kind of turbid material contained in sample water.

The water quality analyzer of the present invention comprises a excitation light irradiating optical system that irradiates sample water to be measured with light source light for excitation, a fluorescence detecting optical system that detects fluorescence of a specific component in sample water excited by irradiation of light source light for excitation, a scattered light irradiating optical system that irradiate sample water with light source light for scattered light detection and a scattered light detecting optical system that detects scattered light scattered by microparticles in sample water by the irradiation with the light source light for scattered light detection, wherein the water quality analyzer configured to detect an amount of the light emitted from the excitation light irradiating optical system and an amount of the light emitted from the scattered light irradiating optical system, and is characterized in that it comprises a transmitted light detecting optical system that can detects a first and a second transmitted lights which are the light source lights for excitation and scattered light detection passed through sample water, and a predict part that calculates the absorbance of the sample water at a first wavelength of light source light for excitation from the first transmitted light and the absorbance of sample water at a second wavelength of light source light for scattered light detection from the second transmitted light, and predicts the absorbance of the sample water at the third wavelength from the absorbances at the first and the second wavelengths.

By this configuration, absorbances of sample water at the first and the second wavelengths are calculated by transmitted light of the light source light for excitation at the first wavelength and transmitted light of the light source light for scattered light detection at the second wavelength. By using these absorbances, the absorbance of the fluorescence having the third wavelength is predicted and the absorbance of the fluorescence having the third wavelength is used for correction of a fluorescence intensity of a component to be measured. Thereby, it is possible to measure the fluorescence intensity with high accuracy and it is also possible to make the configuration of the water quality analyzer simple because it is not required to measure absorbance of sample water at the third wavelength by installing a light source for irradiating the light having the third wavelength for fluorescence intensity correction, and the like in the water analyzer.

In the water quality analyzer of the present invention, absorbance of water sample at the third wavelength is predicted from absolute values of the absorbances of sample water at the first and the second wavelengths and a ration of the absolute values. This configuration makes it possible to predict absorbance at the third wavelength with high accuracy depending on a kind of microparticles in the sample water.

In the water quality analyzer of the present invention, the third wavelength is the peak wavelength of fluorescence spectrum of a specific component in sample water. This configuration makes it possible to enhance the detection efficiency of the fluorescence emitted by the specific component in the sample water that is excited by light source light for excitation.

The water quality analyzer of the present invention comprises a turbidity correction part that calculates a turbidity-corrected fluorescence intensity by correcting the intensity of the fluorescence detected by the fluorescence detecting optical system by using the turbidity measured from the scattered light that is detected by the scattered light detecting optical system. This configuration makes it possible to correct fluorescence intensity of a specific component in sample water effectively in consideration of the effect of the concentration of microparticles in the sample water.

The water quality analyzer of the present invention comprises an absorbance correction part that calculates an absorbance-corrected fluorescence intensity by correcting the turbidity-corrected fluorescence intensity by using the absorbance of the sample water at the first wavelength and the absorbance of the sample water at the third wavelength predicted by the predict part. This configuration makes it possible to correct the fluorescence intensity of the specific component irrespective of the kind of microparticles in the sample water because the effect of the absorbance characteristic can be taken into consideration.

In the water quality analyzer of the present invention, for example, the first wavelength is from 250 to 350 nm, and the second wavelength is from 600 to 900 nm, and the third wavelength is form the first wavelength to the second wavelength. This configuration makes it possible to predict the absorbance at the third wavelength in high accuracy from the absorbance at the first wavelength, a side of shorter wavelength, and the absorbance at the second wavelength, a side of longer wavelength.

The water quality analyzer of the present invention comprises an optical member which guides the light source light for excitation and the light source light for scattered light detection to a sample water passing container and the optical member and the transmitted light detecting optical system are arranged to face each other across the sample water passing container. By this configuration, the optical member can guide the light source light for excitation and the light source light for scattered light detection to the sample water container, and the first transmitted light and the second transmitted light are introduced into the transmitted light detecting optical system appropriately.

The invention claimed is:

1. A water quality analyzer for analyzing sample water, comprising:
    an excitation light irradiating optical system configured to irradiate the sample water with first light, a component in the sample water being excited by the first light to emit fluorescence;
    a scattered light irradiating optical system configured to irradiate the sample water with second light, the second light being scattered by microparticles in the sample water to form scattered light;
    a fluorescence detecting optical system configured to detect a portion of the second light that has passed through the sample water, and to detect the emitted fluorescence; and
    a scattered light detecting optical system configured to detect a portion of the first light that has passed through the sample water, and to detect the scattered light; and
    further comprising:
    a processor; and a non-transitory storage medium having program instructions stored thereon, execution of which by the processor causes the water quality analyzer to
    calculate an absorbance of the sample water at a first wavelength from the portion of the first light that has passed through the sample water,
    calculate an absorbance of the sample water at a second wavelength from the portion of the second light that has passed through the sample water, and predict an absorbance of the sample water at a third wavelength, which is a wavelength of the fluorescence, from the absorbances of the sample water at the first wavelength and the second wavelength.

2. The water quality analyzer according to claim 1, wherein
the excitation light irradiating optical system and the scattered light detecting optical system are arranged so as to be opposed to each other across a sample water passing container, and the scattered light irradiating optical system and the fluorescence detecting optical system are arranged so as to be opposed to each other across the sample water passing container.

3. The water quality analyzer according to claim 2, wherein
at the center of the sample water passing container, an optical axis of the excitation light irradiating optical system and
an optical axis of the fluorescence detecting optical system cross perpendicularly, and an optical axis of the scattered light irradiating optical system and an optical axis of the scattered light detecting optical system cross perpendicularly.

4. The water quality analyzer according to claim 3, wherein
the optical axis of the excitation light irradiating optical system and the optical axis of the fluorescence detecting optical system intersect at a first intersection point, and
the optical axis of the scattered light irradiating optical system and the optical axis of the scattered light detecting optical system intersect at a second intersection point that is separated from the first intersection point in the sample water passing container.

5. The water quality analyzer according to claim 4, wherein
a distance between the first intersection point and the second intersection point is more than 0 mm and no more than 10 mm.

6. The water quality analyzer according to claim 1, wherein the absorbance of the sample water at the third wavelength is predicted from absolute values of the absorbances of the sample water at the first wavelength and the second wavelength and a ratio of the absolute values.

7. A water quality analyzer for analyzing sample water, comprising:
an excitation light irradiating optical system configured to irradiate the sample water with first light, a component in the sample water being excited by the first light to emit fluorescence;
a fluorescence detecting optical system configured to detect the emitted fluorescence;
a scattered light irradiating optical system configured to irradiate the sample water with second light, the second light being scattered by microparticles in the sample water to form the scattered light;
a scattered light detecting optical system configured to detect the scattered light;
a transmitted light detecting optical system configured to detect a portion of the first light that has passed through the sample water and a portion of the second light that has passed through the sample water; and
a processor and a non-transitory storage medium having program instructions stored thereon, execution of which by the processor causes the water quality analyzer to provide a predict part that is configured to
calculate an absorbance of the sample water at a first wavelength from the portion of the first light,
calculate an absorbance of the sample water at a second wavelength from the portion of the second light, and
predict an absorbance of the sample water at a third wavelength, which is a wavelength of the fluorescence, from the absorbances of the sample water at the first wavelength and the second wavelength.

8. The water quality analyzer according to claim 7, wherein
the absorbance of the sample water at the third wavelength is predicted from absolute values of the absorbances of the sample water at the first wavelength and the second wavelength and a ratio of the absolute values.

9. The water quality analyzer according to claim 7, wherein
the third wavelength is a peak wavelength of a fluorescence spectrum of the component in the sample water.

10. The water quality analyzer according to claim 7, wherein the execution of the program instructions by the processor causes the water quality analyzer to further provide a turbidity correction part that corrects intensity of the fluorescence detected by the fluorescence detecting optical system by using a turbidity measured from the scattered light detected by the scattered light detecting optical system, to thereby obtain turbidity-corrected fluorescence intensity.

11. The water quality analyzer according to claim 10, wherein the execution of the program instructions by the processor causes the water quality analyzer to further provide an absorbance correction part that corrects the turbidity-corrected fluorescence intensity by using the absorbance of the sample water at the first wavelength and the absorbance of the sample water at the third wavelength predicted by the predict part, to thereby obtain absorbance-corrected fluorescence intensity.

12. The water quality analyzer according to claim 7, wherein
the first wavelength is equal to or more than 250 nm and equal to or less than 350 nm, the second wavelength is equal to or more than 600 nm and equal to or less than 900 nm, and the third wavelength is equal to or more than the first wavelength and equal to or less than the second wavelength.

13. The water quality analyzer according to claim 7, further comprising an optical member arranged at a position through which the first light and the second light are guided to a sample water passing container, wherein
the optical member and the transmitted light detecting optical system are arranged to be opposed to each other across the sample water passing container.

\* \* \* \* \*